(12) United States Patent  
Wu et al.

(10) Patent No.: US 11,691,150 B2
(45) Date of Patent: Jul. 4, 2023

(54) BIOLOGICAL CHIP, MANUFACTURING METHOD THEREOF, OPERATION METHOD THEREOF, AND BIOLOGICAL DETECTION SYSTEM

(71) Applicants: BEIJING BOE TECHNOLOGY DEVELOPMENT CO., LTD., Beijing (CN); BOE TECHNOLOGY GROUP CO., LTD., Beijing (CN)

(72) Inventors: Zhihong Wu, Beijing (CN); Zijian Zhao, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 557 days.

(21) Appl. No.: 16/753,950

(22) PCT Filed: Sep. 30, 2019

(86) PCT No.: PCT/CN2019/109388
§ 371 (c)(1),
(2) Date: Apr. 6, 2020

(87) PCT Pub. No.: WO2020/073867
PCT Pub. Date: Apr. 16, 2020

(65) Prior Publication Data
US 2021/0205804 A1 Jul. 8, 2021

(30) Foreign Application Priority Data
Oct. 8, 2018 (CN) .......................... 201811167587.X (51) Int. Cl.
*B01L 3/00* (2006.01)
*C12Q 1/6869* (2018.01)

(52) U.S. Cl.
CPC ............ *B01L 3/508* (2013.01); *C12Q 1/6869* (2013.01); *B01L 2200/12* (2013.01);
(Continued)

(58) Field of Classification Search
CPC ................ B01L 3/508; B01L 2200/12; B01L 2300/0819; B01L 2300/12;
(Continued)

(56) References Cited

U.S. PATENT DOCUMENTS 6,203,758 B1    3/2001 Marks et al.
2005/0064581 A1 3/2005 Manalis et al.
(Continued)

FOREIGN PATENT DOCUMENTS

CN    1273364 A    11/2000
CN    1296081 A    5/2001
(Continued)

OTHER PUBLICATIONS

CN 104280365 A (English translation), Double Detection Biological Sensor Chip and Preparation Method Thereof and DNA Detection Method, published Jan. 14, 2015, 11 pages (Year: 2015).*
(Continued)

*Primary Examiner* — Narayan K Bhat
(74) *Attorney, Agent, or Firm* — Dilworth & Barrese, LLP.; Michael J. Musella, Esq.

(57) ABSTRACT

A biological chip, a manufacturing method thereof, an operation method thereof, and a biological detection system are provided. The biological chip includes a base substrate and a plurality of working units. The plurality of the working units are arranged on the base substrate; each of the working units includes a working element configured to be in contact with a target substance; and the working element includes a metal electrode and an electric-field-controllable surface modification layer on a surface of the metal electrode.

19 Claims, 7 Drawing Sheets

(52) U.S. Cl.
CPC ... *B01L 2300/0819* (2013.01); *B01L 2300/12* (2013.01); *B01L 2400/0415* (2013.01)

(58) Field of Classification Search
CPC ..... B01L 2400/0415; B01L 2200/0668; B01L 2300/0645; B01L 2300/0887; B01L 3/502761; C12Q 1/6869; C12Q 2565/629
See application file for complete search history.

(56) References Cited

U.S. PATENT DOCUMENTS

| | | |
|---|---|---|
| 2009/0000957 A1 | 1/2009 | Dubin et al. |
| 2010/0221841 A1 | 9/2010 | Osaka et al. |
| 2011/0117669 A1* | 5/2011 | Ren .................... G01N 27/4145 257/E29.089 |
| 2012/0067742 A1 | 3/2012 | Lee et al. |
| 2019/0099756 A1 | 4/2019 | Pang et al. |

FOREIGN PATENT DOCUMENTS

| | | | |
|---|---|---|---|
| CN | 1963524 A | | 5/2007 |
| CN | 104280365 A | * | 1/2015 |
| CN | 107971049 A | | 5/2018 |
| CN | 109234158 A | | 1/2019 |

OTHER PUBLICATIONS

First Chinese Office Action filed with Chinese Patent Application No. 201811167587.X filed on Apr. 3, 2020.

* cited by examiner

BIOLOGICAL CHIP, MANUFACTURING METHOD THEREOF, OPERATION METHOD THEREOF, AND BIOLOGICAL DETECTION SYSTEM

The present application claims priority of Chinese Patent Application No. 201811167587.X filed on Oct. 8, 2018. For all purposes, the entire disclosure of the aforementioned application is incorporated by reference as part of the disclosure of this application.

TECHNICAL FIELD

Embodiments of the present disclosure relate to a biological chip, a method of manufacturing the biological chip, an operation method of the biological chip, and a biological detection system.

BACKGROUND

With the gradual implementation of human genome (sequencing) project and the development of molecular biology-related disciplines, more and more genome sequences of animals, plants and microorganisms have been determined, and gene sequence data are growing rapidly at an unprecedented rate. Driven by the development of related technologies, gene chip technology emerges. The gene chip technology refers to a technology that conducts a lot of researches on gene expression and monitoring with fluorescent DNA probe based on a principle of base complementary hybridization, in which high-density gene (i.e. DNA) fragments are attached to a solid surface such as a glass sheet in a certain order or arrangement through a certain way by using microarray method.

SUMMARY

At least one embodiment of the present disclosure provides a biological chip, which includes a base substrate; a plurality of working units, arranged on the base substrate; each of the working units comprises a working element configured to be in contact with a target substance, and the working units comprise a metal electrode and an electric-field-controllable surface modification layer on a surface of the metal electrode away from the base substrate and facing the target substance.

For example, in the biological chip provided by at least one embodiment of the present disclosure, the electric-field-controllable surface modification layer comprises an electric-field-controllable isomerized organic molecule, and an end of the electric-field-controllable isomerized organic molecule is connected to the surface of the metal electrode.

For example, in the biological chip provided by at least one embodiment of the present disclosure, the electric-field-controllable isomerized organic molecule includes a thioglycolic acid or a thioglycolic acid derivative molecule, and the thioglycolic acid or the thioglycolic acid derivative molecule is connected to the surface of the metal electrode through a mercapto group at an end of the thioglycolic acid or the thioglycolic acid derivative molecule.

For example, in the biological chip provided by at least one embodiment of the present disclosure, a material of the metal electrode includes at least one of gold and silver.

For example, the biological chip provided by at least one embodiment of the present disclosure further includes a flow channel defining layer arranged on the base substrate, the flow channel defining layer includes a flow channel, and a fluid comprising the target substance reaches at least one of the plurality of working units through the flow channel.

For example, in the biological chip provided by at least one embodiment of the present disclosure, the flow channel includes side walls arranged opposite to each other, the side walls arranged opposite to each other constitute a plurality of branches, and the plurality of the branches are crossed and communicated at intersections.

For example, in the biological chip provided by at least one embodiment of the present disclosure, each of the working units further includes a switching element, the switching element includes a control end, a first end, and a second end, and the working element is electrically connected with the second end of the switching element, and the switching element is configured to determine whether to apply a working voltage to the working element according to a control signal.

For example, in the biological chip provided by at least one embodiment of the present disclosure, the base substrate is a glass substrate.

For example, in the biological chip provided by at least one embodiment of the present disclosure, the target substance includes a gene fragment, and the gene fragment is fixed on the working element.

For example, in the biological chip provided by at least one embodiment of the present disclosure, an end group of the gene fragment includes one or more of a mercapto group, an amino group, a hydroxyl group, a carboxyl group, a phosphate group, an alkoxy group, an amine group, a fluorinated group, a quaternary amine group and a quaternary phosphor group.

For example, the biological chip provided by at least one embodiment of the present disclosure further includes an opposite substrate, the opposite substrate is disposed opposite to the base substrate, and the working unit is located between the opposite substrate and the base substrate.

For example, in the biological chip provided by at least one embodiment of the present disclosure, the opposite substrate includes an opposite base and an opposite electrode, and the opposite electrode is disposed on a surface of the opposite base opposite to the base substrate and the opposite electrode is opposite to the working units.

For example, the biological chip provided by at least one embodiment of the present disclosure further includes a flow channel defining layer arranged on the base substrate, the flow channel defining layer includes a flow channel, the flow channel comprises side walls arranged opposite to each other, and the side walls are abutted against the opposite substrate.

At least one embodiment of the present disclosure further provides a biological detection system, which includes a controller unit and the biological chip in any one of the embodiments of the present disclosure, and the controller unit is configured to apply a control signal to the plurality of the working units of the biological chip.

At least one embodiment of the present disclosure further provides a method of manufacturing a biological chip, which includes: forming a plurality of working units on a base substrate, in which each of the working units includes a working element for contacting with a target substance, and the working element includes a metal electrode and an electric-field-controllable surface modification layer formed on a surface of the metal electrode away from the base substrate and facing the target substance; applying a control signal to a selected working unit of the plurality of the working units, and forming a control electric field through the working element of the selected working unit, in which the control electric field controls a property of the electric-field-controllable surface modification layer of the working element of the selected working unit to control an operation of a fluid including the target substance.

At least one embodiment of the present disclosure further provides an operation method of any one of the biological chips mentioned above, which includes: applying a control signal to a selected working unit of the plurality of the working units, and forming a control electric field through a working element of the selected working unit, in which the control electric field controls a property of the electric-field-controllable surface modification layer of the working element of the selected working unit to control an operation of a fluid including the target substance.

For example, in the operation method of the biological chip provided by at least one embodiment of the present disclosure, the control electric field causes the electric-field-controllable isomerized organic molecule in the electric-field-controllable surface modification layer to lie on the surface of the metal electrode, the electric-field-controllable surface modification layer exhibits hydrophobicity; if the target substance is located on the electric-field-controllable surface modification layer, the target substance is spaced apart from the metal electrode, and the target substance flows on the electric-field-controllable surface modification layer.

For example, in the operation method of the biological chip provided by at least one embodiment of the present disclosure, the control electric field causes the electric-field-controllable isomerized organic molecule in the electric-field-controllable surface modification layer to stand up on the surface of the metal electrode, the electric-field-controllable surface modification layer exhibits hydrophilicity; if the target substance is located on the electric-field-controllable surface modification layer, the target substance is in contact with the metal electrode, and the target substance is connected to the surface of the metal electrode through an end portion of the target substance.

BRIEF DESCRIPTION OF THE DRAWINGS

In order to clearly illustrate the technical solution of the embodiments of the present disclosure, the drawings of the embodiments will be briefly described. It is apparent that the described drawings are only related to some embodiments of the present disclosure and thus are not limitative of the present disclosure.

DETAILED DESCRIPTION

In order to make objects, technical details and advantages of embodiments of the present disclosure clear, the technical solutions of the embodiments will be described in a clearly and fully understandable way in connection with the related drawings. It is apparent that the described embodiments are just a part but not all of the embodiments of the present disclosure. Based on the described embodiments herein, those skilled in the art can obtain, without any inventive work, other embodiment(s) which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the description and claims of the present disclosure, are not intended to indicate any sequence, amount or importance, but distinguish various components. Similarly, the terms "a," "an," or "the," etc., are not intended to indicate the limitation to quantity, but rather indicate that there is at least one. The terms "comprises," "comprising," "includes," "including," etc., are intended to specify that the elements or the objects stated before these terms encompass the elements or the objects listed after these terms as well as equivalents thereof, but do not exclude other elements or objects. The phrases "connect", "connected", etc., are not intended to define a physical connection or a mechanical connection, but may comprise an electrical connection which is direct or indirect. The terms "on," "under," "right," "left" and the like are only used to indicate relative position relationship, and in a case that the position of an object is described as being changed, the relative position relationship may be changed accordingly.

Single nucleotide polymorphism (SNP) chip is a type of gene chip. The SNP chip is usually implemented by using a structure of combining microwells with microspheres, that is, oligonucleotides with addresses and probes are connected to glass microspheres by amino groups firstly, then the glass microspheres with different addresses are filled into the microwells. Herein, "address" refers to a sequence of the oligonucleotides, different sequences represent different addresses, and the oligonucleotides are usually short-stranded nucleotides that contain bases with a number less than 20.

It is difficult to control the distribution position of the microsphere structure of the SNP chip manufactured by the method mentioned above, that is, it is difficult to control the distribution position of gene segments (such as probes), thus the distribution of the gene fragments is very random. Therefore, it is necessary to detect the oligonucleotide sequence used as an address of each microsphere structure in advance in order to know the corresponding probe sequence on the microsphere structure. The distribution information of these probes needs to be provided to the users for later comparison in a case that the chip is used for genetic testing, thus labor cost and time cost are increased. In addition, the SNP chips are usually manufactured based on microwell or nanowell technology, and most of them use silicon-based materials, so the production cost of the SNP chips is very high. Due to the use of microsphere structures to graft oligonucleotide fragments, the production cost is further increased.

At least one embodiment of the present disclosure provides a biological chip, its manufacturing method, its operation method, and a biological detection system. The biological chip realizes the controllability of a fixed position of gene fragments, reduces a problem such as fluorescence crosstalk between gene fragments, and the manufacturing method of the biological chip is compatible with semiconductor preparation process, so its production cost is low, which helps to improve the detection accuracy and detection throughput.

In the following, the embodiments of the present disclosure will be described in detail with reference to the drawings. It should be noted that, same reference numerals in different drawings will be used to refer to the same elements described.

At least one embodiment of the present disclosure provides a biological chip, and the biological chip includes a base substrate and a plurality of working units. The plurality of the working units are arranged on the base substrate, each of the working units includes a working element for contacting with a target substance, and the working element comprises a metal electrode and an electric-field-controllable surface modification layer provided on a surface of the metal electrode away from the base substrate.

Figure 1:
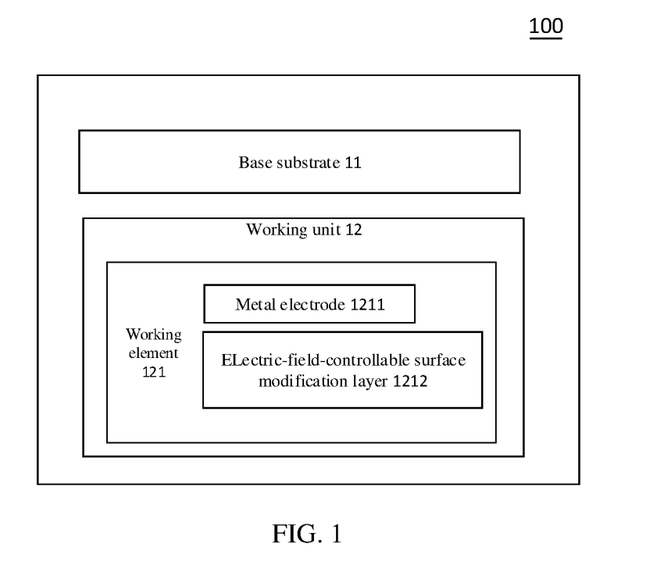
FIG. 1 is a block schematic diagram of a biological chip provided by embodiments of the present disclosure.

FIG. 1 is a block schematic diagram of the biological chip provided by the embodiments of the present disclosure. As shown in FIG. 1, the biological chip 100 includes a base substrate 11 and a plurality of working units 12. For example, the plurality of the working units 12 are arranged on the base substrate 11. Each of the working units 12 includes a working element 121, the working element 121 is used for contacting with a target substance. The working element 121 includes a metal electrode 1211 and an electric-field-controllable surface modification layer 1212 provided on a surface of the metal electrode 1211 away from the base substrate 11. For example, the target substance is gene fragments, the gene fragments include oligonucleotides, primers, probes, target DNA fragments or polypeptides, etc., which are not limited in embodiments of the present disclosure. For example, different gene fragments are fixed on different working elements 121 among the plurality of the working elements 121 so that the controllability of the position of the gene fragments is achieved. The biological chip 100 fixed with the gene fragments is used to detect substances containing genes to be detected. For example, the genes to be detected are detected by base complementary hybridization of the gene fragments fixed on the working element 121 with the genes to be detected, such as performing gene sequencing and so on. The biological chip 100 is applied in a field of biomolecule detection and other related fields.

Figure 2:
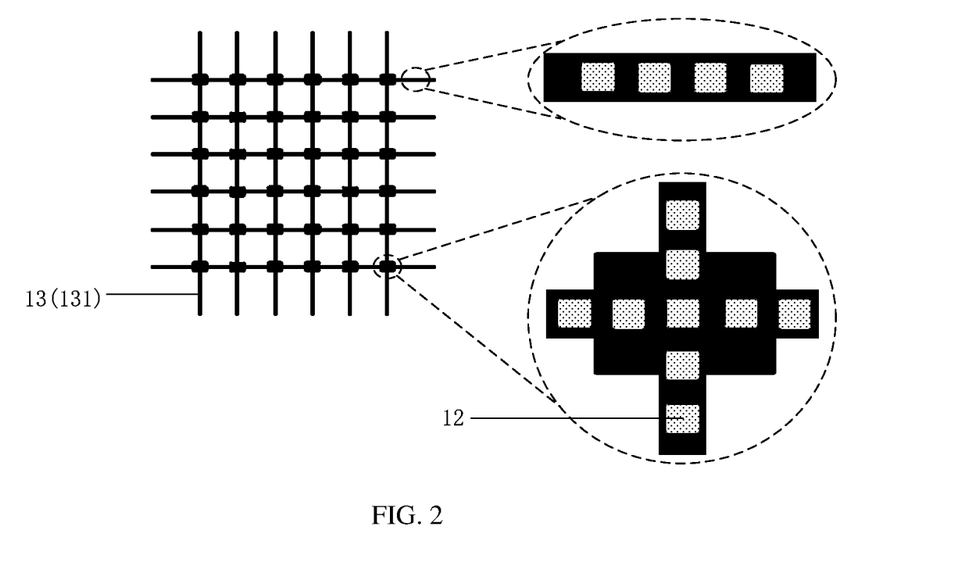
FIG. 2 is a distribution schematic diagram of a flow channel of the biological chip provided by the embodiments of the present disclosure.
Figure 3:
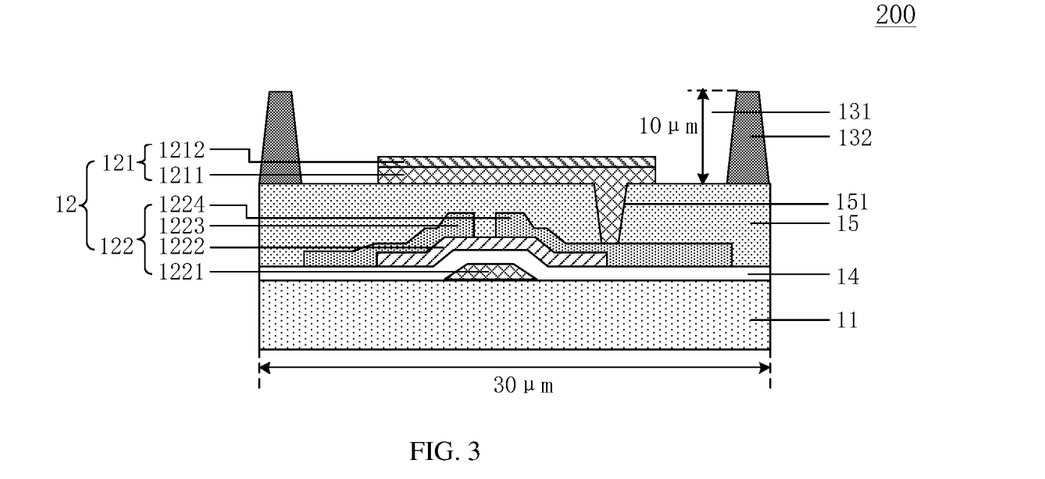
FIG. 3 is a sectional schematic diagram of the biological chip provided by the embodiments of the present disclosure.

FIG. 2 is a distribution schematic diagram of a flow channel of the biological chip provided by the embodiments of the present disclosure; FIG. 3 is a sectional schematic diagram of the biological chip provided by the embodiments of the present disclosure. As shown in FIG. 2 and FIG. 3, the biological chip 200 includes a flow channel defining layer 13 arranged on the base substrate 11, the flow channel defining layer 13 defines a flow channel 131, and the flow channel 131 helps to limit fluid including the target substance on the base substrate 11, for example, a flow direction and a droplet size of the fluid. The plurality of the working units 12 are distributed along the flow channel 131, for example, the plurality of the working units 12 are uniformly or non-uniformly distributed along the flow channel 131. The total number of the working units 12 in the biological chip 200 is not limited, and the total number ranges from 50,000 to 10,000,000, or other quantity, which is not limited in the embodiments of the present disclosure. For example, in an example, the plurality of the working units 12 are arranged in an array, the array includes 100 rows and 100 columns, and the total number of the working units 12 is 10,000.

For example, the flow channel 131 provides a flow channel for the fluid (for example a liquid droplet) including the target substance, which allows the fluid including the target substance to flow through the flow channel 131 and to reach at least one of the plurality of the working units 12. For example, the fluid including the target substance is controlled to flow along the flow channel 131 and reach a predetermined working unit 12, then the target substance (that is the gene fragments) is controlled to be fixed on the working element 121 of the predetermined working unit 12, so that the fixed position of the gene fragments is controllable (how to drive the fluid to flow and how to fix the gene fragments will be described in detail later).

For example, the flow channel 131 includes a plurality of branches. For example, in an example, as shown in FIG. 2, the plurality of the branches are crossed and are communicated at each of intersections, and the plurality of the working units 12 are distributed along the plurality of the branches. In this way, the branches are spread over the entire base substrate 11, and the fluid including the target substance is able to reach any one of the working units 12 through the branches. Of course, the embodiments of the present disclosure are not limited to this, for example, the branches are distributed in any ways, such as a plurality of concentric circles, a plurality of concentric rectangles, etc., and the distribution of the branches are determined according to actual requirements.

As shown in FIG. 3, in the biological chip 200, the working units 12 are disposed on the base substrate 11 and are located in the flow channel 131. For example, each of the working units 12 includes the working element 121 and a switching element 122 which are electrically connected with each other, the working element 121 is arranged on the switching element 122, and the working element 121 is located in the flow channel 131 and is exposed inside the flow channel 131, so that the working element 121 is in contact with the fluid flowing through the flow channel 131.

For example, the base substrate 11 plays a role of supporting, protecting, etc., and the base substrate 11 is a glass substrate, a plastic substrate, a quartz substrate or a substrate made of other suitable materials, which is not limited in the embodiments of the present disclosure. Because the biological chip 200 is compatible with conventional semiconductor manufacturing processes, compared with ordinary biological chips (such as SNP chips) using silicon based substrates, the substrates made of the materials mentioned above allow that the production cost of the biological chip 200 is effectively reduced.

The switching element 122 is arranged on the base substrate 11, and the switching element 122 is configured to determine whether to apply a working voltage to the working element 121 according to a control signal. For example, the switching element 122 is a three-end element such as a thin film transistor, and the switching element 122 includes a control end, a first end, and a second end. For example, the control terminal is a gate electrode 1221, the first end is a first electrode 1223, and the second end is a second electrode 1224. In addition, the switching element 122 further includes an active layer 1222.

The gate electrode 1221 is disposed on the base substrate 11, and the gate electrode 1221 is made of metal, transparent conductive material, or other suitable materials. A gate insulating layer 14 is disposed on the base substrate 11, and the gate insulating layer 14 covers the gate electrode 1221. The gate insulating layer 14 is made of silicon nitride, silicon oxide, or other suitable materials.

The active layer 1222 is disposed on the gate insulating layer 14, and the active layer 1222 is used to provide a channel region. In addition, the active layer 1222 is made of a polysilicon semiconductor material, for example, a low temperature polysilicon semiconductor material, a high temperature polysilicon semiconductor material, or the active layer 1222 is made of other suitable materials, for example, an oxide semiconductor material, such as indium zinc gallium oxide IGZO, which is not limited in the embodiments of the present disclosure.

The first electrode 1223 and the second electrode 1224 are disposed on the gate insulating layer 14 and are respectively overlapped with two ends of the active layer 1222. For example, the first electrode 1223 and the second electrode 1224 are symmetrically arranged, so the positions of the two electrodes are interchangeable. For example, the first electrode 1223 is a source electrode or a drain electrode, and accordingly, the second electrode 1224 is the drain electrode or the source electrode. Both the first electrode 1223 and the second electrode 1224 are made of any suitable metals or alloy of the suitable metals such as gold, silver, copper, aluminum and the like, which is not limited in the embodiments of the present disclosure.

It should be noted that, in the embodiments of the present disclosure, the switching element 122 is not limited to the thin film transistor, and the switching element 122 may be a field effect transistor or other devices having similar characteristics. In a case that the switching element 122 is the thin film transistor, the switching element 122 is a bottom-gate thin film transistor or a top-gate thin film transistor. In addition, in order to improve the performance of the switching element 122, the biological chip 200 further includes other layers such as a light shielding layer, a buffer layer, etc., and the arrangement of these layers may refer to the conventional design, which is omitted herein.

Figure 4:
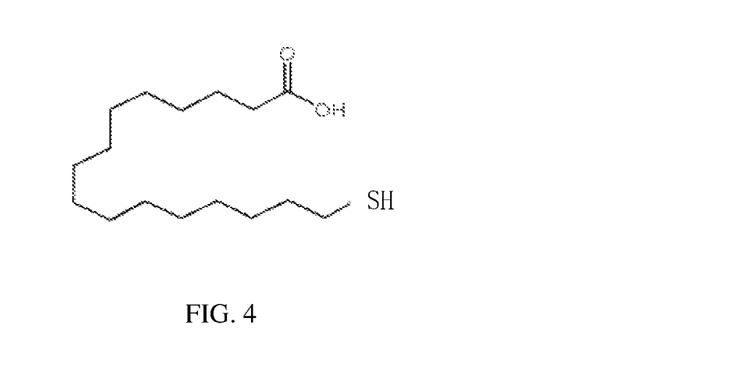
FIG. 4 is a schematic diagram of a molecular structure of thiohexadecanolic acid.

For example, the working element 121 is disposed on a passivation layer 15, and the passivation layer 15 covers the first electrode 1223 and the second electrode 1224 of the switching element 122. The working element 121 includes a metal electrode 1211 and an electric-field-controllable surface modification layer 1212 provided on a surface of the metal electrode 1211. For example, the metal electrode 1211 is electrically connected with the second end (the second electrode 1224) of the switching element 122 through a via hole 151 penetrating the passivation layer 15. For example, the metal electrode 1211 is made of gold, silver, or other suitable metals. For example, the electric-field-controllable surface modification layer 1212 includes an electric-field-controllable isomerized organic molecule, and an end of the electric-field-controllable isomerized organic molecule is connected with the surface of the metal electrode 1211. For example, the electric-field-controllable isomerized organic molecule is a thioglycolic acid (such as a thiohexadecanolic acid, the molecular structure of which is shown in FIG. 4) or a thioglycolic acid derivative molecule. In a case that the metal electrode 1211 is made of gold or silver, the thioglycolic acid or the thioglycolic acid derivative molecule is chemically bonded with a metal atom (or ion) in the metal electrode 1211 through the mercapto group at the end of the thioglycolic acid or the thioglycolic acid derivative molecule to form a covalent bond, so that the thioglycolic acid or thioglycolic acid derivative molecule is connected with the surface of the metal electrode 1211.

The flow channel 131 is disposed on the passivation layer 15 and includes side walls 132 arranged opposite to each other. For example, the U-shaped grooves formed by the side walls 132 arranged opposite to each other and the passivation layer 15 constitute the flow channel 131 and its branches, thereby providing a flow path for the fluid (e.g., a liquid droplet) including the target substance. The working element 121 is located between the side walls 132 arranged opposite to each other so as to be in contact with the liquid droplet including the target substance. For example, a material of the side walls 132 is a photosensitive organic material such as a photoresist, which is not only easy to manufacture, but also has a lower cost. For example, the flow channel 131 has a height of 10 μm and a width of 30 μm, that is, the height of the side walls 132 is 10 μm, and the distance between the side walls 132 arranged opposite to each other is 30 μm. It should be noted that, in the embodiments of the present disclosure, the material of the side walls 132 is not limited to the photosensitive organic material such as the photoresist, and other suitable materials may also be used. The height of the side walls 132 and the distance between the side walls 132 arranged opposite to each other are not limited, the height of the side walls 132, for example, is from 8 μm to 12 μm, and the distance between the opposite side walls 132, for example, is from 25 μm to 35 μm, which depends on actual requirements.

For example, in an example, the side walls 132 are manufactured by exposing and developing the photoresist (model: KMH-T546). For example, the photoresist is spinning coated on the passivation layer 15 at 300 revolutions per minute (RPM) (a thermal weight loss temperature is 320° C.), and pre-baked for 2 minutes at 90° C., and the spinning coating is repeated once; then the photoresist is exposed into a target pattern by using a mask, in which the exposure intensity is 999 mJ and the exposure time is 15 seconds; then the photoresist is developed with a developing solution for 45 seconds, and then the photoresist is solidified at a temperature of 230° C. for 30 minutes, so that the side walls 132 are obtained. For example, the height of the obtained side walls 132 is 9.8 μm. It should be noted that, the above process for manufacturing the side walls 132 is only exemplary and not restrictive, the side walls 132 may be manufactured by any suitable processes.

For example, in an example, the gate electrode 1221 of the switching element 122 is connected with a scanning line (not shown in figures) arranged separately, and the first electrode 1223 of the switching element 122 is connected with a driving line (not shown in figures) arranged separately. The scanning line is used to apply the control signal to the gate electrode 1221 (the control end) of the switching element 122 to control the turning on or off of the switching element 122, and the driving line is used to apply the working voltage to the first electrode 1223 (the first end) of the switching element 122, so that the switching element 122 applies the working voltage to the working element 121 according to the control signal. For example, in a case that the control signal is valid, the switching element 122 is turned on, the working voltage received by the first electrode 1223 is transmitted to the second electrode 1224 and is further transmitted to the metal electrode 1211 of the working element 121, and the magnitude of the working voltage applied to the metal electrode 1211 is controlled by adjusting the magnitude of the working voltage transmitted through the driving line. In a case that the control signal is invalid, the switching element 122 is turned off, so that the metal electrode 1211 of the working element 121 does not receive the working voltage. In this way, whether the working voltage is applied to the working element 121 or not is determined according to the control signal, and the magnitude of the working voltage is adjustable. For example, the scanning line is connected with a controller unit provided separately, and the driving line is connected with a controller unit or a digitally controllable voltage source that is separately provided, so that the control signal and the working voltage are received respectively by the scanning line and the driving line.

For example, in an example, in a case that the plurality of the working units 12 located on the base substrate 11 are arranged in an array, that is, in a case that the plurality of the switching elements 122 are arranged in an array, the gate electrodes 1221 of the switching elements 122 in a same row are connected with a same scanning line, and the first electrodes 1223 of the switching elements 122 in a same row are connected with a same driving line, thereby the total number of the electrical lines is reduced. Of course, the embodiments of the present disclosure are not limited to this, and the scanning line and the driving line may be arranged separately for each of the switching elements 122, in this way, each of the switching elements 122 is controlled independently and is not affected by adjacent switching elements 122 in the same row or in the same column, so that the combination of the turning on or off states of the plurality of the switching elements 122 is diversified.

It should be noted that, in the embodiments of the present disclosure, the biological chip 200 may further include more or fewer components, the relative positional relationship of the components is not limited, which is dependent on actual requirements. For example, the biological chip 200 further includes an opposite substrate, the buffer layer, the light shielding layer, etc., thereby more additional functions are provided, so that the performance of the biological chip 200 is improved.

Figure 5:
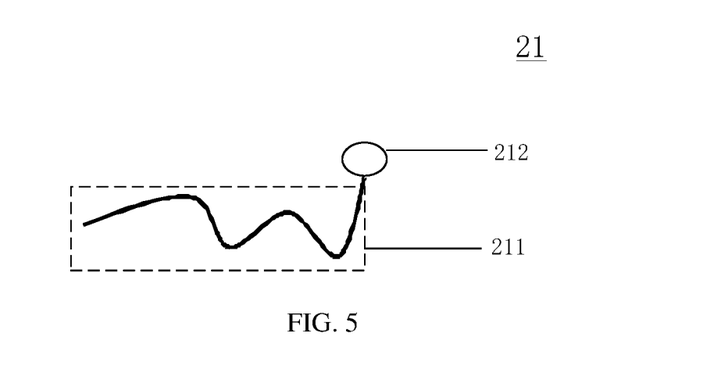
FIG. 5 is a schematic diagram of a target substance of the biological chip provided by the embodiments of the present disclosure.

In this biological chip 200, for example, the working element 121 is in contact with the target substance 21, and the target substance 21 is fixed on the working element 121. For example, as shown in FIG. 5, the target substance 21 is a gene fragment, the gene fragment includes a functional fragment 211 and an end group 212. For example, the functional fragment 211 is an oligonucleotide, a primer, a probe, a target DNA fragment or a polypeptide, etc., which is not limited in the embodiments of the present disclosure. For example, in a case that the functional fragment 211 is the probe, the functional fragment 211 performs base complementary hybridization with the gene to be detected, so that the gene to be detected is detected. For example, the end group 212 is a mercapto group, which is obtained by modifying the functional fragment 211 with the use of cysteine ($C_3H_7NO_2S$). In a case that the metal electrode 1211 is made of gold or silver, the mercapto group is chemically bonded with the metal atom (or ion) of the metal electrode 1211 to form the covalent bond, so that the target substance 21 (that is the gene fragment) is connected with the surface of the metal electrode 1211, so as to achieve the fixation of the gene fragment. For example, the end group of the gene fragment further includes one or more of an amino group, a hydroxyl group, a carboxyl group, a phosphate group, an alkoxy group, an amine group, a fluorine-containing group, a quaternary amine group, and a quaternary phosphorus group.

It should be noted that, the shape of the target substance 21 (that is the gene fragment) shown in FIG. 5 is only schematic, which does not represent the actual shape of the gene fragment. In addition, a size ratio relationship between the end group 212 and the functional fragment 211 in the figure is only for more clearly showing and explaining, which does not represent the actual size ratio relationship.

The electric-field-controllable surface modification layer 1212 is obtained by modifying the metal electrode 1211 by using the electric-field-controllable isomerized organic molecule, that is, the electric-field-controllable surface modification layer 1212 includes the electric-field-controllable isomerized organic molecule. For example, in an example, the metal electrode 1211 is modified by using the thiohexadecanolic acid, thereby forming the covalent bond by chemically bonding the mercapto group at the end of the thiohexadecanolic acid with the metal atom (or ion) in the metal electrode 1211, so that the thiohexadecanolic acid is connected with the surface of the metal electrode 1211 to form the electric-field-controllable surface modification layer 1212. For example, the electric-field-controllable isomerized organic molecule includes thioglycolic acid (such as thiohexadecanolic acid) or thioglycolic acid derivative molecules, these molecules have mercapto groups at their ends, in order to facilitate connection with the metal electrode 1211.

It should be noted that, in the embodiments of the present disclosure, the type of the electric-field-controllable isomerized organic molecule is not limited, and may be a molecule of any suitable substance. The group at the end of the electric controllable isomerized organic molecule is not limited to the mercapto group, and may be one or more of an amino group, a hydroxyl group, a carboxyl group, a phosphate group, an alkoxy group, an amine group, a fluorine-containing group, a quaternary amine group and a quaternary phosphorus group, which is not limited in the embodiments of the present disclosure. All of the groups are connected with the metal electrodes 1211 of corresponding metal materials, so as to achieve the corresponding functions.

Figure 6A:
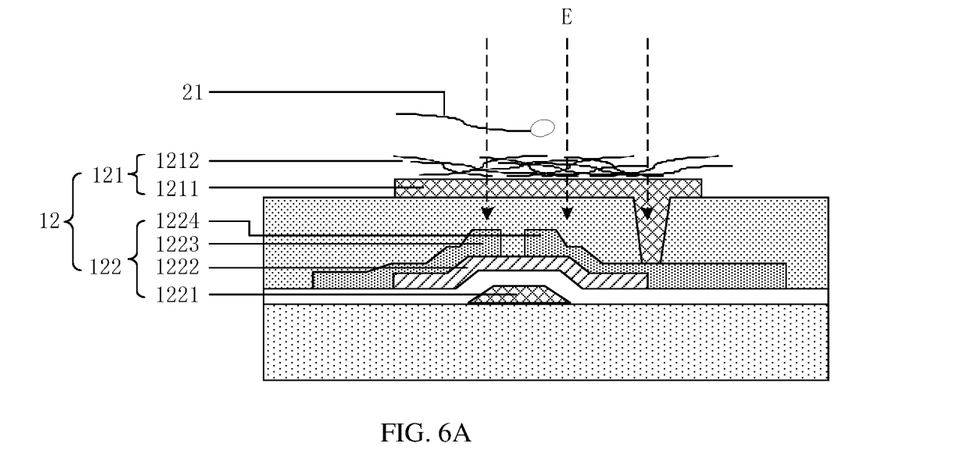
FIG. 6A and FIG. 6B are state schematic diagrams of an electric-field-controllable surface modification layer of the biological chip provided by the embodiments of the disclosure.
Figure 6B:
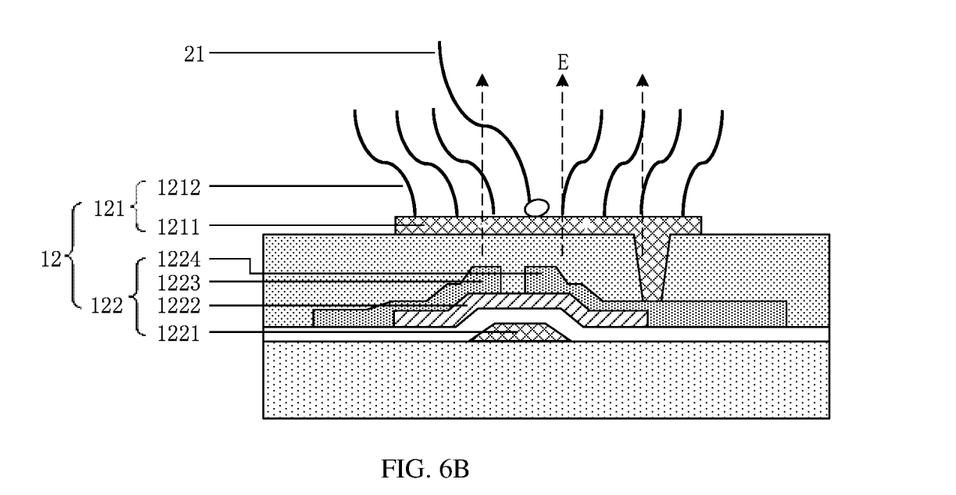

The hydrophilicity/hydrophobicity of the electric-field-controllable surface modification layer 1212 is changed according to the direction of the applied control electric field. For example, in an example, in a case that the direction of the control electric field E applied to the electric-field-controllable surface modification layer 1212 is a direction indicated by an arrow in FIG. 6A, the electric-field-controllable isomerized organic molecule in the electric-field-controllable surface modification layer 1212, for example, lies on the surface of the metal electrode 1211, which facilitates the flow of the liquid. In this case, under the action of the control electric field E, the electric-field-controllable surface modification layer 1212 exhibits hydrophobicity; if the target substance 21 is located on the electric-field-controllable surface modification layer 1212, the target substance 21 cannot be in contact with the metal electrode 1211, and the target substance 21 flows on the electric-field-controllable surface modification layer 1212. In a case that the direction of the control electric field E applied to the electric-field-controllable surface modification layer 1212 is shown in FIG. 6B, the electric-field-controllable isomerized organic molecule in the electric-field-controllable surface modification layer 1212, for example, stand up on the surface of the metal electrode 1211, which facilitates that the liquid stays. In this case, under the action of the control electric field E, the electric-field-controllable surface modification layer 1212 exhibits hydrophilicity; if the target substance 21 is located on the electric-field-controllable surface modification layer 1212, the target substance 21 can be in contact with the metal electrode 1211, and the target substance 21 is connected with the surface of the metal electrode 1211 through the mercapto group at the end.

For example, the positive or negative property of the working voltage applied to the metal electrode 1211 is controlled to form the control electric field E with a separately arranged common electrode for providing a common voltage, and the direction of the control electric field E is determined by the positive or negative property of the working voltage and the relative positional relationship between the common electrode and the metal electrode 1211. For example, the scope of the control electric field E is not limited to the region where the metal electrode 1211 and the common electrode directly face each other, and the scope of the control electric field E for example is further extended to a region outside the region where the metal electrode 1211 and the common electrode directly face each other by controlling the magnitude of the working voltage. Therefore, for example, the common electrode is arranged on the base substrate 11 and under the working element 121, or the common electrode is arranged on other components (such as the opposite substrate) other than the base substrate 11 and is opposite to the metal electrode 1211.

The working principle of the biological chip 200 is described in the following.

Figure 7:
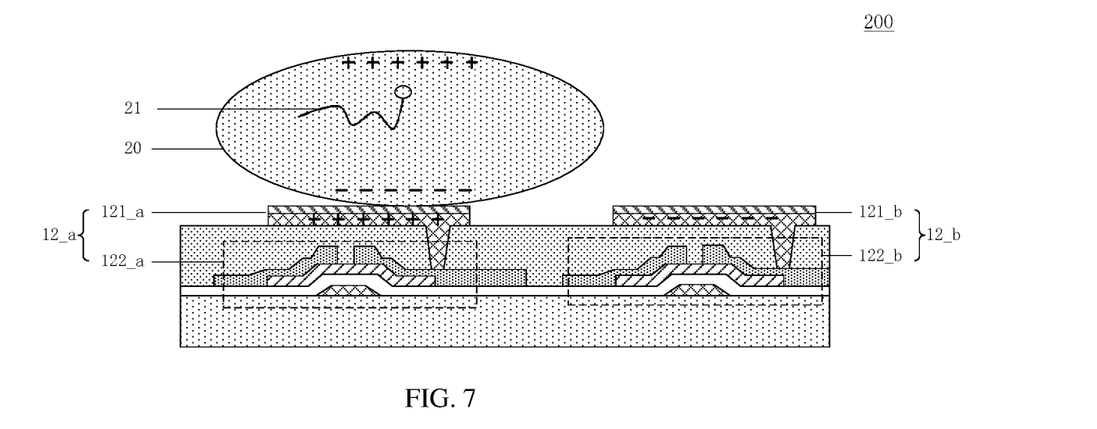
FIG. 7 is a schematic diagram of a flow of the target substance of the biological chip provided by the embodiments of the present disclosure.

As shown in FIG. 7, the first working unit 12_a and the second working unit 12_b are two adjacent working units located in the flow channel 131, the liquid droplet 20 is located in the flow channel 131 and includes the target substance 21. For example, the liquid droplet 20 is driven from one working unit 12 to another working unit 12 by an electro-wetting method (for example, the liquid droplet 20 flows from the first working unit 12_a to the second working unit 12_b), so that the liquid droplet 20 flows between a plurality of working units 12, and the liquid droplet 20 is capable of reaching any one of the working units 12. For example, by controlling the working voltage applied to the working element 121 of the working unit 12 adjacent to the liquid droplet 20, the corresponding electric-field-controllable surface modification layer 1212 is controlled to exhibit hydrophilicity or hydrophobicity and the degree of the hydrophilicity or hydrophobicity is controlled as well, and the polarity of the charge on the surface of the metal electrode 1211 of the working unit 12 adjacent to the liquid droplet 20 is controlled, so that the liquid droplet 20 flows or stays.

For example, in an example, as shown in FIG. 7, a first voltage and a valid control signal are applied to the first switching element 122_a of the first working unit 12_a, so that the voltage of the first working element 121_a is the first voltage; and a second voltage and a valid control signal are applied to the second switching element 122_b of the second working unit 12_b, so that the voltage of the second working element 121_b is the second voltage. For example, the first voltage is a positive voltage, the second voltage is a negative voltage, and the absolute value of the negative voltage is small. For example, the biological chip 200 further includes a common electrode (not shown in FIG. 7), the common electrode is disposed on the base substrate 11 and is located below the first working element 121_a and the second working element 121_b, and the common electrode is used to provide a common voltage for all of the working units 12, for example, non-metal conductive materials such as poly-silicon, indium zinc oxide, or suitable metal materials are used to form the common electrode. The direction of the control electric field E formed by the first working element 121_a is the same as the direction of the electric field shown in FIG. 6A, and the direction of the control electric field E formed by the second working element 121_b is the same as the direction of the electric field shown in FIG. 6B. At this time, the electric-field-controllable surface modification layer in the first working element 121_a is hydrophobic, and the electric-field-controllable surface modification layer in the second working element 121_b exhibits weak hydrophilicity.

The surface of the metal electrode in the first working element 121_a accumulates positive charges under the action of the first voltage, a side of the liquid droplet 20 that is in contact with the first working element 121_a accumulates negative charges, accordingly, a side of the liquid droplet 20 away from the first working element 121_a accumulates positive charges. The second working element 121_b adjacent to the liquid droplet 20 accumulates negative charges under the action of the second voltage, thus the side of the liquid droplet 20 away from the first working element 121_a has an attraction effect with the second working element 121_b, so that the liquid droplet 20 is caused to roll. As a result, the liquid droplet 20 flows from the first working unit 12_a to the second working unit 12_b, thereby the flow of the liquid droplet 20 is realized. Because the hydrophilicity of the electric-field-controllable surface modification layer in the second working element 121_b is extremely weak, the target substance 21 in the liquid droplet 20 is not influenced.

Before the liquid droplet 20 reaches the predetermined working element 121, the plurality of the electric-field-controllable surface modification layers 1212 located in a flow path of the liquid droplet 20 exhibit hydrophobic as a whole by applying a positive working voltage; and the liquid droplet 20 flows along the flow path by making a small adjustment to the working voltage (for example, applying a small negative voltage to the working elements 121 adjacent to the liquid droplet 20 in turn). Once the liquid droplet 20 reaches the predetermined working element 121, a negative voltage having a relatively large absolute value is applied to the predetermined working element 121, and the corresponding electric-field-controllable surface modification layer 1212 exhibits hydrophilicity, so that the target substance 21 in the liquid droplet 20 is fixed on the surface of the corresponding metal electrode 1211. In this way, the target substance 21 is fixed on the predetermined working element 121, and the correspondence between the target substance 21 and the fixed position is clearly determined; in a case that the target substance 21 is the probe, the sequence of the probe on each of the working elements 121 is clearly known, which facilitates the subsequent detection and analysis.

It should be noted that, in the embodiments of the present disclosure, the positive or negative property and the magnitude of the working voltage applied to each of the working elements 121 are determined according to actual requirements, which are not limited in the embodiments of the present disclosure; for example, the positive or negative property and the magnitude are determined according to the direction of the control electric field E to be formed, as long as the liquid droplet 20 is controlled to flow and the target substance 21 in the liquid droplet 20 is fixed on the predetermined working element 121.

For example, the formation of the liquid droplet 20 is achieved by adding a surfactant (i.e., polyethylene glycol (PEG)) to an aqueous phase. Before the liquid droplet 20 enters the flow channel 131, the flow channel 131 of the biological chip 200 is filled with a bovine serum albumin (BSA) solution with a mass fraction of 0.2%, and the flow channel 131 is soaked for 1 hour to reduce the adsorption of the target substance 21 to the inner surface of the flow channel 131, and then, the BSA solution is pumped out by a micropump.

For example, an active matrix composed of a plurality of the switching elements 122 is used to control the working voltages applied to the working elements 121 of the plurality of the working units 12, so that the liquid droplet 20 containing the target substance 21 flows to the predetermined working element 121 by means of the electro-wetting method as described above. For example, in an example, a plurality of the liquid droplets 20 containing different target substances 21 are caused to flow in different branches respectively, and the flow paths of the liquid droplets 20 do not cross each other, so that the plurality of the liquid droplets 20 including the different target substances 21 are controlled to flow to the respective predetermined working elements 121. Thus, the time cost is effectively saved by this multi-channel approach.

By the way mentioned above, the biological chip 200 realizes the control of the fixed position of the target substance 21 (that is the gene fragment); in a case that a user uses the biological chip 200, the user only needs to know the position of the detection point so that the uses knows the sequence of the corresponding target substance 21, which is convenient and quick. For example, it is also possible to make the fixed positions of different target substances 21 far apart from each other, so that the problem such as fluorescence crosstalk between the target substances 21 is alleviated and the detection accuracy is improved after the target substance 21 is hybridized with the gene to be detected. The biological chip 200 is convenient for subsequent image analysis and recognition, which helps to increase the detection throughput. In addition, because the fixed position of the target substance 21 is controlled, the total number of the operation steps is reduced; for example, compared with the conventional chip using the microwell and microsphere structure, the sequencing step after fixing the gene fragment is omitted. For example, the biological chip 200 is able to fix a primer for amplification and sequencing, which has multiple functions. The biological chip 200 is compatible with the semiconductor manufacturing process, for example, a common display panel manufacturing process is used for manufacture the biological chip 200, and the production cost is low, which is suitable for mass production.

Figure 8:
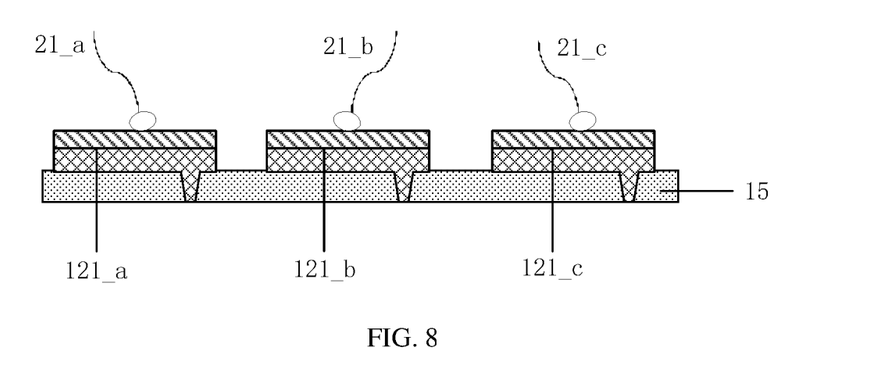
FIG. 8 is a schematic diagram of a fixed position of the target substance of the biological chip provided by the embodiments of the present disclosure.

For example, different target substances 21 are fixed to the plurality of the working elements 121 to increase the detection throughput. For example, as shown in FIG. 8, a first target substance 21_a, a second target substance 21_b, and a third target substance 21_c are respectively fixed on the first working element 121_a, the second working element 121_b, and the third working element 121_c, and the first target substance 21_a, the second target substance 21_b, and the third target substance 21_c are different from each other. The total number of types of the target substance 21 is smaller than or equal to the total number of the working elements 121. In the same biological chip 200, the more types of the target substance 21 are, the larger the detection throughput is.

Figure 9:
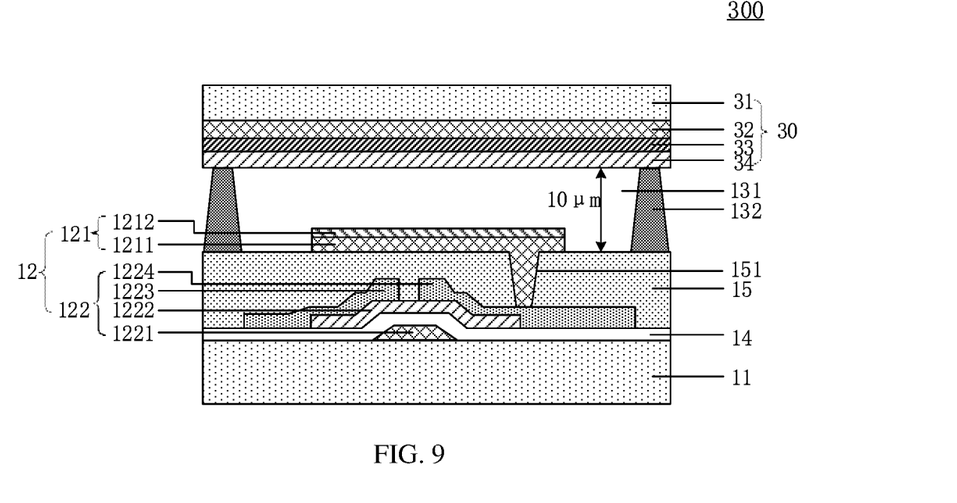
FIG. 9 is another sectional schematic diagram of the biological chip provided by the embodiments of the present disclosure.

FIG. 9 is another sectional schematic diagram of the biological chip provided by the embodiments of the present disclosure. As shown in FIG. 9, except for that the biological chip further includes an opposite substrate 30 comprising an opposite base 31, an opposite electrode 32, a dielectric layer 33, and a hydrophobic layer 34, the biological chip 300 shown in FIG. 9 is basically the same as the biological chip 200 shown in FIG. 3.

In the embodiment shown in FIG. 9, the opposite substrate 30 is disposed opposite to the base substrate 11, and the working unit 12 is located between the opposite substrate 30 and the base substrate 11. The opposite base 31 plays a role of supporting and protecting, and the opposite electrode 32 is provided on the opposite base 31. The opposite base 31 is a glass substrate, a plastic substrate, a quartz substrate, or a substrate made of other suitable materials, which is not limited in the embodiments of the present disclosure.

The opposite electrode 32 is arranged on a surface of the opposite base 31 opposite to the base substrate 11 and is disposed opposite to the working unit 12. The opposite electrode 32, for example, is the common electrode for providing the common voltage, so that the control electric field is formed between the opposite electrode 32 and the metal electrode 1211. For example, the plurality of the opposite electrodes 32 corresponding to the plurality of the working units 12 are connected as a whole, that is, the opposite electrode 32 covers a region, corresponding to the plurality of the working units 12, of the opposite substrate 31 to simplify the production process and facilitate the processing. For example, the opposite electrode 32 is made of any suitable materials, such as a metal or a transparent conductive material, which is not limited in the embodiments of the present disclosure.

For example, the side walls 132 are abutted against the opposite substrate 30 to maintain a distance between the passivation layer 15 and the opposite substrate 30, and the side walls 132 play a support function of the opposite substrate 30.

The dielectric layer 33 is arranged on a surface of the opposite electrode 32 opposite to the base substrate 11 and has a function of insulation, for example, the dielectric layer 33 is made of a material such as silicon dioxide and the like. The hydrophobic layer 34 is disposed on a surface of the dielectric layer 33 opposite to the base substrate 11, and a closed space is formed by the hydrophobic layer 34, the side walls 132 arranged opposite to each other and the passivation layer 15, in order to form the flow channel 131 and the plurality of the branches, so that a flow path for the liquid droplet 20 is provided. Because the flow channel 131 is closed, the biological chip 300 is not easily affected by the external environment and has strong anti-interference ability. The hydrophobic layer 34 is hydrophobic, in order to prevent the target substance 21 in the liquid droplet 20 from adhering to the surface of the hydrophobic layer 34, avoiding the waste of the target substance 21, and the hydrophobic layer 34 facilitates the flow of the liquid droplets 20. For example, the hydrophobic layer 34 is made of any suitable material such as silicon nitride and the like. For example, the distance between the hydrophobic layer 34 and the passivation layer 15 is 10 μm.

Figure 10:
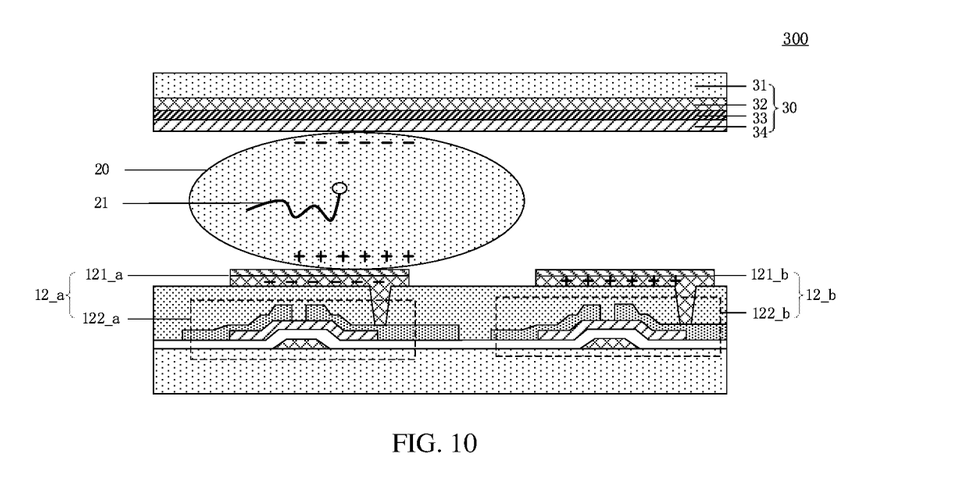
FIG. 10 is another schematic diagram of the flow of the target substance of the biological chip provided by the embodiments of the present disclosure.

The working principle of the biological chip 300 is similar to the working principle of the biological chip 200. As shown in FIG. 10, the first working unit 12_a and the second working unit 12_b are two adjacent working units located in the flow channel 131, and the liquid droplet 20 is located in the flow channel 131 and includes the target substance 21. For example, a third voltage and a valid control signal are applied to the first switching element 122_a of the first working unit 12_a, so that the voltage of the first working element 121_a is the third voltage; a fourth voltage and a valid control signal are applied to the second switching element 122_b of the second working unit 12_b, so that the voltage of the second working element 121_b is the fourth voltage. For example, the third voltage is a negative voltage, the fourth voltage is a positive voltage, and the absolute value of the fourth voltage is small. The common electrode 32 is provided with the common voltage, for example, the common electrode 32 is grounded. At this time, the direction of the control electric field E formed by the first working element 121_a is the same as the direction of the electric field shown in FIG. 6A, and the direction of the control electric field E formed by the second working element 121_b is the same as the direction of the electric field shown in FIG. 6B. Therefore, the electric-field-controllable surface modification layer in the first working element 121_a exhibits hydrophobicity, and the electric-field-controllable surface modification layer in the second working element 121_b exhibits weak hydrophilicity.

Because the surface of the metal electrode in the first working element 121_a accumulates negative charges under the action of the third voltage, the side where the liquid droplet 20 is in contact with the first working element 121_a accumulates positive charges, accordingly, the side of the liquid droplet 20 away from the first working element 121_a accumulates negative charges. The second working element 121_b adjacent to the liquid droplet 20 accumulates positive charges under the action of the fourth voltage, so that the side of the liquid droplet 20 away from the first working element 121_a has an attraction effect with the second working element 121_b, so that the liquid droplet 20 is driven to roll. As a result, the liquid droplet 20 flows from the first working unit 12_a to the second working unit 12_b, so that the flow of the liquid droplets 20 is realized. Because the hydrophilicity of the electric-field-controllable surface modification layer in the second working element 121_b is extremely weak, the target substance 21 in the liquid droplet 20 will be not affected.

Once the liquid droplet 20 flows to the predetermined working element 121, a positive voltage with a relatively large absolute value is applied to the predetermined working element 121, which makes the electric-field-controllable surface modification layer 1212 of the predetermined working element 121 exhibit hydrophilicity, so that the target substance 21 in the liquid droplet 20 is fixed on the surface of the metal electrode 1211 of the predetermined working element 121.

It should be noted that, in the embodiments of the present disclosure, the positive or negative property and the magnitude of the working voltage applied to the working element 121 are determined according to actual requirements, which are not limited in the embodiments of the present disclosure, for example, depending on the direction of the control electric field E to be formed, as long as the liquid droplet 20 is controlled to flow.

The biological chip 300 realizes the controllability of the fixed position of the gene fragment, reduces the problem such as fluorescence crosstalk between gene fragments, and the biological chip 300 is compatible with the semiconductor manufacturing process so that its production cost is low, which helps to improve the detection accuracy and detection throughput.

At least one embodiment of the present disclosure further provides a biological detection system including the biological chip in any one of the above embodiments of the present disclosure. The biological detection system realizes the controllability of the fixed position of the gene fragment, reduces the problem such as fluorescence crosstalk between gene fragments, and the biological chip is compatible with the semiconductor manufacture process so that its production cost is low, which helps to improve the detection accuracy and detection throughput.

Figure 11:
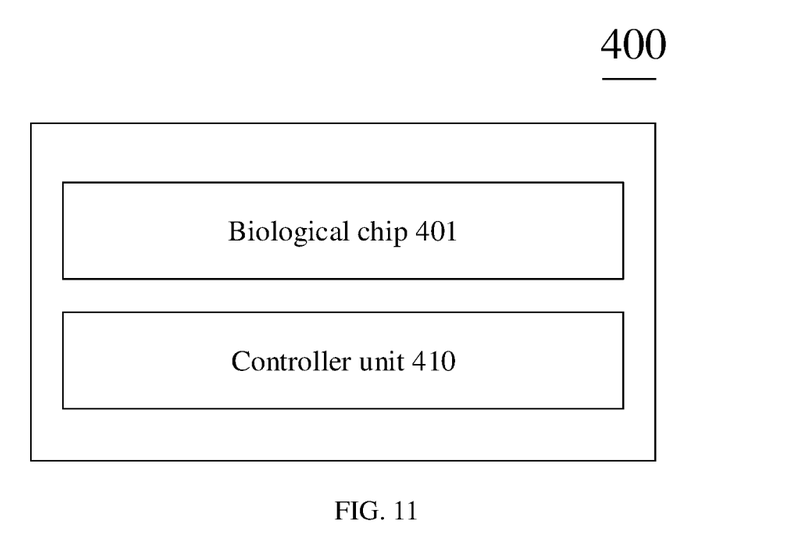
FIG. 11 is a block schematic diagram of a biological detection system provided by the embodiments of the present disclosure.

FIG. 11 is a block schematic diagram of the biological detection system provided by the embodiments of the present disclosure. As shown in FIG. 11, the biological detection system 400 includes a biological chip 401, the biological chip 401 is the biological chip in any one of the embodiments of the present disclosure, for example, the biological chip 100/200/300 mentioned above. The biological detection system 400 further includes a controller unit 410, the controller unit 410 is configured to apply the control signal to the plurality of working units 12 in the biological chip 401. For example, the controller unit 410 applies the control signal to cause the liquid droplet 20 containing the target substance 21 to flow in the flow path 131 of the biological chip 401, and to cause the liquid droplet 20 to reach the predetermined working unit 12 and be fixed on the corresponding working element 121, so that the user uses the biological chip 401 to detect the genes to be detected. For example, the controller unit 410 is configured to provide the working voltage so that an additional voltage source is omitted. For example, the controller unit 410 is implemented as a dedicated or general electronic hardware (or a circuit), which is not limited in the embodiments of the present disclosure. The specific composition of the above electronic hardware is not limited, and for example includes an analog device, a digital chip, or other applicable devices.

At least one embodiment of the present disclosure further provides a method of manufacturing the biological chip; by using the manufacturing method, the biological chip in any one of the embodiments of the present disclosure is manufactured. By using the manufacturing method, the biological chip realizes the controllability of the fixed position of the gene fragment, reduces the problem such as fluorescence crosstalk between gene fragments, and the biological chip is compatible with the semiconductor preparation process so that its production cost is low, which helps to improve the detection accuracy and detection throughput.

Figure 12:
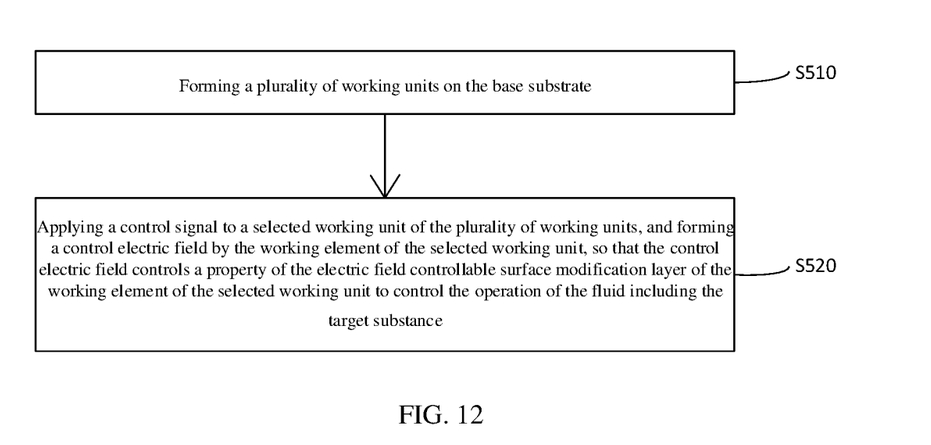
FIG. 12 is a schematic flowchart of a method of manufacturing the biological chip provided by an embodiment of the present disclosure.

FIG. 12 is a schematic flowchart of the method of manufacturing the biological chip provided by at least one embodiment of the present disclosure. For example, in an example, as shown in FIG. 12, the method for manufacturing the biological chip includes the following operations.

Step S510: forming a plurality of working units 12 on the base substrate 11;

Step S520: applying a control signal to a selected working unit 12 of the plurality of working units 12, and forming a control electric field by the working element 121 of the selected working unit 12, so that the control electric field controls a property of the electric-field-controllable surface modification layer 1212 of the working element 121 of the selected working unit 12 to control the operation of the fluid including the target substance 21.

For example, each of the working units 12 includes the working element 121 for contacting the target substance 21, and the working element 121 includes the metal electrode 1211 and the electric-field-controllable surface modification layer 1212 formed on the surface of the metal electrode 1211.

For example, the operation for controlling the fluid including the target substance 21 includes: driving the fluid to flow through the selected working unit 12 or fixing the target substance 21 in the fluid on the working element 121 of the selected working unit 12.

It should be noted that, the detailed descriptions and technical effects of the manufacturing method of the biological chip may refer to the corresponding descriptions of the biological chip 100/200/300 in the above embodiments of the present disclosure, which is omitted herein.

At least one embodiment of the present disclosure also provides an operation method of the biological chip; by using the operation method, the biological chip in any one of the above embodiments of the present disclosure is used. By using the operation method, the biological chip realizes the controllability of the fixed position of the gene fragment, reduces the problem such as fluorescence crosstalk between gene fragments, and the biological chip is compatible with the semiconductor preparation process so that its production cost is low, which helps to improve the detection accuracy and detection throughput.

For example, the operation method of the biological chip includes: applying the control signal to the selected working unit 12 of the plurality of working units 12, and forming the control electric field by the working element 121 of the selected working unit 12, so that the control electric field controls the property of the electric-field-controllable surface modification layer 1212 of the working element 121 of the selected working unit 12 to control the operation of the fluid including the target substance 21.

For example, the operation for controlling the fluid including the target substance 21 includes: driving the fluid to flow through the selected working unit 12 or fixing the target substance 21 in the fluid on the working element 121 of the selected working unit 12.

It should be noted that, the detailed descriptions and technical effects of the operation method of the biological chip may refer to the corresponding descriptions of the biological chip 100/200/300 in the above embodiments of the present disclosure, which is omitted herein.

The following points required to be explained:

(1) the drawings of the embodiments of the present disclosure only relate to the structures related to the embodiments of the present disclosure, and other structures may refer to the general design.

(2) without conflict, the embodiments of the present disclosure and the features in the embodiments may be combined with each other to obtain new embodiments. What are described above is related to only the illustrative embodiments of the present disclosure and not limitative to the protection scope of the present application. Therefore, the protection scope of the present application shall be defined by the accompanying claims.

What is claimed is:

1. A biological chip, comprising:
    a base substrate;
    a plurality of working units, arranged on the base substrate;
    a flow channel defining layer, arranged on the base substrate;
    wherein each of the working units comprises a working element configured to be in contact with a target substance, and the working element comprises a metal electrode and an electric-field-controllable surface modification layer on a surface of the metal electrode away from the base substrate and facing the target substance;
    the flow channel defining layer comprises a flow channel, and a fluid comprising the target substance reaches at least one of the plurality of working units through the flow channel.

2. The biological chip according to claim 1, wherein the electric-field-controllable surface modification layer comprises an electric-field-controllable isomerized organic molecule, and an end of the electric-field-controllable isomerized organic molecule is connected to the surface of the metal electrode.

3. The biological chip according to claim 2, wherein the electric-field-controllable isomerized organic molecule comprises a thioglycolic acid or a thioglycolic acid derivative molecule, and the thioglycolic acid or the thioglycolic acid derivative molecule is connected to the surface of the metal electrode through a mercapto group at an end of the thioglycolic acid or the thioglycolic acid derivative molecule.

4. The biological chip according to claim 1, wherein a material of the metal electrode comprises at least one of gold and silver.

5. The biological chip according to claim 1, wherein the flow channel comprises side walls arranged opposite to each other, the side walls arranged opposite to each other constitute a plurality of branches, and the plurality of the branches are crossed and communicated at intersections.

6. The biological chip according to claim 1, wherein each of the working units further comprises a switching element, the switching element comprises a control end, a first end, and a second end, and the working element is electrically connected with the second end of the switching element, and the switching element is configured to determine whether to apply a working voltage to the working element according to a control signal.

7. The biological chip according to claim 1, wherein the base substrate is a glass substrate.

8. The biological chip according to claim 1, wherein the target substance comprises a gene fragment, and the gene fragment is fixed on the working element.

9. The biological chip according to claim 8, wherein an end group of the gene fragment comprises one or more of a mercapto group, an amino group, a hydroxyl group, a carboxyl group, a phosphate group, an alkoxy group, an amine group, a fluorinated group, a quaternary amine group and a quaternary phosphor group.

10. The biological chip according to claim 1, further comprising an opposite substrate, wherein the opposite substrate is disposed opposite to the base substrate, and the working unit is located between the opposite substrate and the base substrate.

11. The biological chip according to claim 10, wherein the opposite substrate comprises an opposite base and an opposite electrode, and the opposite electrode is disposed on a surface of the opposite base opposite to the base substrate and the opposite electrode is opposite to the working units.

12. The biological chip according to claim 10, wherein the flow channel comprises side walls arranged opposite to each other, and the side walls are abutted against the opposite substrate.

13. A biological detection system, comprising a controller unit and the biological chip according to claim 1, wherein the controller unit is configured to apply a control signal to the plurality of the working units of the biological chip.

14. A method of manufacturing a biological chip, comprising:
    forming a plurality of working units on a base substrate, wherein each of the working units comprises a working element for contacting with a target substance, and the working element comprises a metal electrode and an electric-field-controllable surface modification layer formed on a surface of the metal electrode away from the base substrate and facing the target substance;

forming a flow channel defining layer on the base substrate, wherein the flow channel defining layer comprises a flow channel, and a fluid comprising the target substance reaches at least one of the plurality of the working units through the flow channel;

applying a control signal to a selected working unit of the plurality of the working units, and forming a control electric field through the working element of the selected working unit, wherein the control electric field controls a property of the electric-field-controllable surface modification layer of the working element of the selected working unit to control an operation of a fluid including the target substance.

15. An operation method of the biological chip according to claim 1, comprising:

applying a control signal to a selected working unit of the plurality of the working units, and forming a control electric field through the working element of the selected working unit, wherein the control electric field controls a property of the electric-field-controllable surface modification layer of the working element of the selected working unit to control an operation of a fluid including the target substance.

16. The operation method according to claim 15, wherein the electric-field-controllable surface modification layer comprises an electric-field-controllable isomerized organic molecule, the control electric field causes the electric-field-controllable isomerized organic molecule in the electric-field-controllable surface modification layer to lie on the surface of the metal electrode, the electric-field-controllable surface modification layer exhibits hydrophobicity;

if the target substance is located on the electric-field-controllable surface modification layer, the target substance is spaced apart from the metal electrode by the electric-field-controllable surface modification layer, and the target substance flows on the electric-field-controllable surface modification layer.

17. The operation method according to claim 15, wherein the electric-field-controllable surface modification layer comprises an electric-field-controllable isomerized organic molecule, the control electric field causes the electric-field-controllable isomerized organic molecule in the electric-field-controllable surface modification layer to stand up on the surface of the metal electrode, the electric-field-controllable surface modification layer exhibits hydrophilicity;

if the target substance is located on the electric-field-controllable surface modification layer, the target substance is in contact with the metal electrode, and the target substance is connected to the surface of the metal electrode through an end portion of the target substance.

18. The biological chip according to claim 11, wherein the flow channel comprises side walls arranged opposite to each other, and the side walls are abutted against the opposite substrate.

19. The biological chip according to claim 11, wherein the opposite substrate further comprises a dielectric layer and a hydrophobic layer, the dielectric layer is arranged on a surface of the opposite electrode opposite to the base substrate, and the hydrophobic layer is disposed on a surface of the dielectric layer opposite to the base substrate.

* * * * *

UNITED STATES PATENT AND TRADEMARK OFFICE
CERTIFICATE OF CORRECTION

| | | |
|---|---|---|
| PATENT NO. | : 11,691,150 B2 | Page 1 of 1 |
| APPLICATION NO. | : 16/753950 | |
| DATED | : July 4, 2023 | |
| INVENTOR(S) | : Zhihong Wu and Zijian Zhao | |

It is certified that error appears in the above-identified patent and that said Letters Patent is hereby corrected as shown below:

On the Title Page (73) Assignees Should read: BEIJING BOE TECHNOLOGY DEVELOPMENT CO., LTD., Beijing (CN); BOE TECHNOLOGY GROUP CO., LTD., Beijing (CN)

Signed and Sealed this
Seventeenth Day of September, 2024

Katherine Kelly Vidal
*Director of the United States Patent and Trademark Office*